US009788988B2

(12) United States Patent
Kompa

(10) Patent No.: US 9,788,988 B2
(45) Date of Patent: Oct. 17, 2017

(54) HINGE FOR ORTHOPEDIC DEVICES

(75) Inventor: Joshua J. Kompa, Trabuco Canyon, CA (US)

(73) Assignee: OSSUR HF, Reykjavik (IS)

( * ) Notice: Subject to any disclaimer, the term of this patent is extended or adjusted under 35 U.S.C. 154(b) by 750 days.

(21) Appl. No.: 12/877,429

(22) Filed: Sep. 8, 2010

(65) Prior Publication Data
US 2012/0059296 A1 Mar. 8, 2012

(51) Int. Cl.
A61F 5/01 (2006.01)

(52) U.S. Cl.
CPC .......... A61F 5/0123 (2013.01); A61F 5/0102 (2013.01); A61F 2005/0137 (2013.01); A61F 2005/0165 (2013.01); A61F 2005/0167 (2013.01)

(58) Field of Classification Search
CPC ...... A61F 2/00; A61F 2/30; A61F 2/38; A61F 2/3804; A61F 2/3836; A61F 2/384; A61F 2/3845; A61F 2/50; A61F 2/54; A61F 2/58; A61F 2/582; A61F 2/60; A61F 2/604; A61F 2/64; A61F 2/68; A61F 5/00; A61F 5/01; A61F 5/0102; A61F 5/0123; A61F 5/0125; A61F 5/013; A61F 5/37; A61F 5/3715; A61F 5/3723; A61F 5/373; A61F 2005/0132; A61F 2005/0165; A61F 2005/0167
USPC ...... 602/5, 16, 20, 23, 26, 27; 128/846, 869, 128/878, 881, 882
See application file for complete search history.

(56) References Cited

U.S. PATENT DOCUMENTS

| | | |
|---|---|---|
| 3,901,223 A | 8/1975 | May |
| 4,723,539 A | 2/1988 | Townsend |
| 4,821,707 A | 4/1989 | Audette |
| 4,886,054 A | 12/1989 | Castillo et al. |
| 4,890,607 A | 1/1990 | Townsend |
| 5,022,391 A | 6/1991 | Weidenburner |
| 5,259,832 A | 11/1993 | Townsend et al. |
| 5,288,287 A | 2/1994 | Castillo et al. |
| 7,044,925 B2 | 5/2006 | Castillo et al. |

(Continued)

FOREIGN PATENT DOCUMENTS

WO 2004/078078 A1 9/2004

OTHER PUBLICATIONS

International Search Report and Written Opinion issued in PCT/US2011/050171, dated Nov. 25, 2011, 8 pages.

Primary Examiner — Keri J Nelson
(74) Attorney, Agent, or Firm — Workman Nydegger

(57) ABSTRACT

A hinge for an orthopedic device includes an upper hinge component having a bottom peripheral surface defined by a first geometrical configuration, and a lower hinge component having a top peripheral surface defined by a second geometrical configuration. An outer plate pivotally connects at first location points to the upper and lower hinge components, and a rear component pivotally connects at second location points to the upper and lower hinge components. The hinge has a rotation stop defining a third geometrical configuration defining a top portion corresponding in shape to at least a portion of the bottom peripheral surface and is arranged to directly abut the portion of the bottom peripheral surface. The rotation stop also defines a bottom portion corresponding in shape to at least a portion of the top peripheral surface and is arranged to directly abut the portion of the top peripheral surface.

21 Claims, 7 Drawing Sheets

(56) References Cited

U.S. PATENT DOCUMENTS

| | | |
|---|---|---|
| 7,235,058 B2 | 6/2007 | Doty et al. |
| 7,544,174 B2 | 6/2009 | Nathanson |
| 8,287,476 B2 * | 10/2012 | Bettiol .......................... 602/16 |
| 2006/0009722 A1 | 1/2006 | Seligman |
| 2006/0173392 A1 | 8/2006 | Turrini et al. |
| 2008/0082031 A1 * | 4/2008 | Nathanson ................. 602/16 |
| 2008/0249630 A1 * | 10/2008 | Brunneke ................ 623/19.12 |
| 2009/0299244 A1 | 12/2009 | Chiang et al. |

* cited by examiner

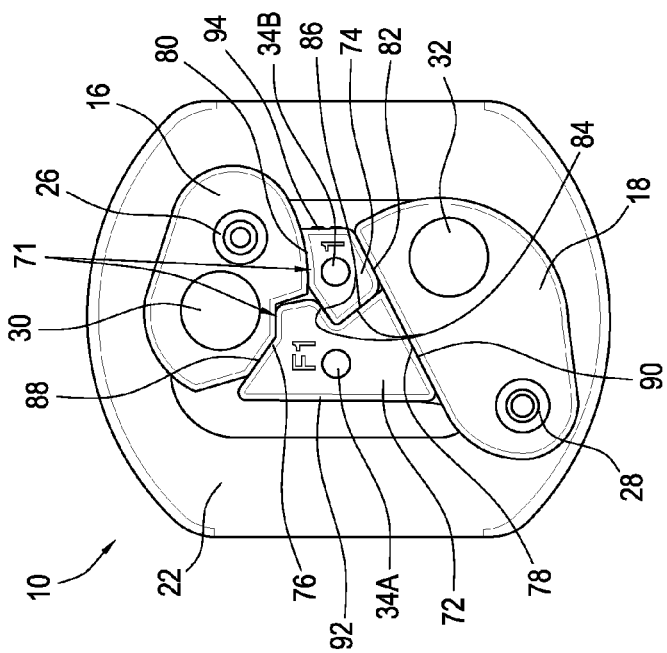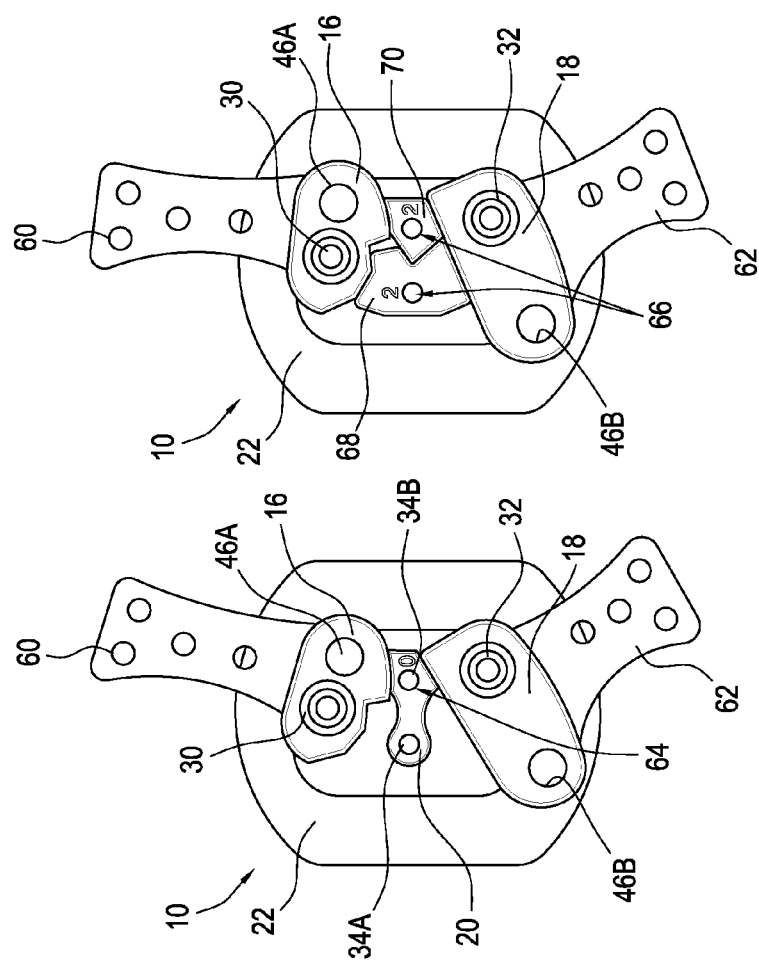

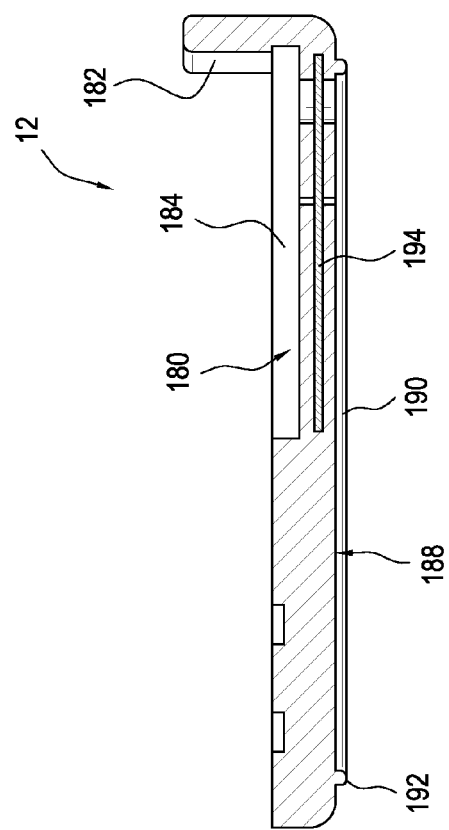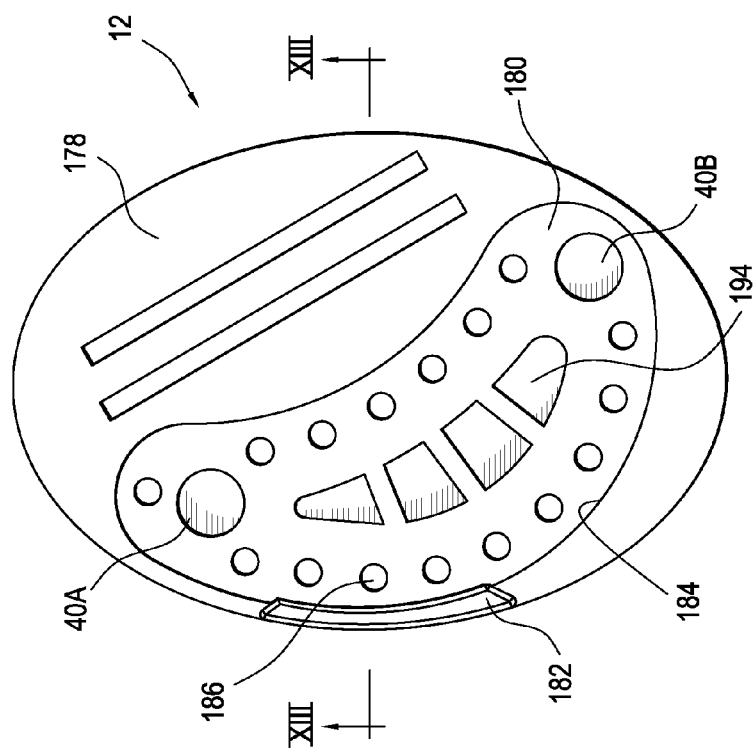

HINGE FOR ORTHOPEDIC DEVICES

FIELD OF THE INVENTION

The present invention relates to orthopedic devices, and more specifically to orthopedic devices for supporting joints, and controlling and limiting joint movement.

BACKGROUND

Many types of orthopedic devices include hinges that serve to support joints, and control and limit joint movements. These joints include the knee, elbow, shoulder, hip, ankle and wrist joints.

The knee joint, although frequently considered a hinge joint, comprises two joints, lateral and medial, between the femur and tibia, and one arthrodial joint between the patella and femur. The primary movements of the knee comprise flexion, i.e., rearward rotational movement of the tibia relative the femur, and extension, i.e. forward rotational movement of the tibia relative the femur.

The flexion and extension movements of the knee joint are not simply pivotal movements about a fixed axis. During flexion, the axis around which movement takes place shifts backward, and during extension it shifts forward. This is different from a more typical hinge joint, such as an elbow, where the axis of rotation does not shift. As full extension is reached, the tibia is rotated inward or rearward and the joint in effect is disposed in a "locked" position with the ligaments taut. This gives the joint greater stability in the extended position. As flexion is initiated, the tibia initially lowers or moves downwardly with small external rotation of the tibia unlocking the joint and subsequently the tibia rotates or rolls about the joint to full flexion. Accordingly, the initial unlocking of the knee joint during flexion precedes actual full rotation of the knee.

Because of the complexity associated with knee movement as described above, a knee brace hinge mechanism must be able to simulate the movements of the knee. The incorporation of such hinge mechanism is crucial, as the knee brace must optimally support the knee joint of its user.

In the context of post-surgical applications, the requirement for such simulation of the knee joint is essential in order to rehabilitate and prevent re-injury of an injured knee joint. Additionally, the hinge mechanism should also be able to control the range of knee joint flexion and extension so that the knee is not reinjured due to hyperextension or flexion. As the optimal range of knee joint motion may vary between users and change during the progress of rehabilitation, the knee brace hinge mechanism used in conjunction with such surgical applications should further be adjustable to correspond to the particular motion range of the user's leg.

In recognizing the need for an effective post-surgical knee brace, various types of hinge mechanisms have been incorporated into known knee braces for post-surgical applications. However, most conventional hinge mechanisms typically fail to provide the precise simulation of knee joint movement or control the range of knee joint motion. Such deficiencies inevitably decrease the likelihood of the user's knee joint from being properly rehabilitated after surgery. Further, some known knee brace hinge mechanisms fail to possess sufficient adjustability so as to quickly and easily provide the optimal set range of knee motion depending upon the current user's needs and rehabilitation progress.

In view of the shortcomings of conventional knee brace hinge mechanisms; there exists a substantial need in the art for a hinge system that can closely simulate the motion of the knee joint while regulating the range of its flexion and extension. More specifically, it is desirable to provide a hinge system that can be easily and quickly adjusted so as to provide a variable, optimal range of knee joint flexion and extension for the particular need of its user.

Many contemporary knee braces fail to provide the precise simulation of knee joint movement or have comprised relatively heavy, bulky apparatus, thereby detracting from the user's athletic endeavor. Further, known designs fail to possess sufficient structural integrity to prevent re-injury of the knee joint as may be occasioned by impact to the knee joint during physical sport endeavors.

The features of the present invention are provided in recognition of the need for orthopedic braces and hinges components for use that are streamlined, low profile, and easy to adjust while effectively supporting joints, and controlling and limiting joint movement. This recognition is realized with the invention described hereinafter.

SUMMARY

In accordance with an embodiment of the invention, a hinge for an orthopedic device includes an upper hinge component having a bottom peripheral surface defined by a first geometrical configuration, and a lower hinge component having a top peripheral surface defined by a second geometrical configuration. An outer plate pivotally connects at first location points to the upper and lower hinge components, and a rear component pivotally connects at second location points to the upper and lower hinge components.

The hinge also includes a rotation stop having a third geometrical configuration defining a top portion corresponding in shape to at least a portion of the bottom peripheral surface and is arranged to directly abut the portion of the bottom peripheral surface. The rotation stop also defines a bottom portion corresponding in shape to at least a portion of the top peripheral surface and is arranged to directly abut the portion of the top peripheral surface.

The third geometrical configuration of the rotation stop may be configured and dimensioned so as to lie within the width of the second geometrical configuration of the lower hinge component, and the top peripheral surface may be arranged as a substantially linear surface. This configuration of the rotation stop allows for improved engagement with the peripheral surfaces of the upper and lower hinge components, while maintaining the rotation stop confined within the confines hinge (as opposed to being externally mounted or partially externally mounted on the hinge).

The rotation stop is preferably mounted to the rear component at a plurality of locations, for example, two third location points, so as to eliminate the possibility of rotation of the rotation stop upon abutment by one of the upper or lower hinge components. Thus, according to a variation, the first rotation stop defines first and second apertures, and first and second fasteners secure the rotation stop to the rear component at the third location points.

The hinge may include a cover secured to and located adjacent to the outer plate. A flange is preferably arranged on a forward side of the hinge, and extends to the rear component so as to protect the internal components of the hinge. The cover may define a clearance between the rear component on a rear side of the hinge, and can serve to provide access to the rotation stop.

According to a variation, the cover defines a recess receiving the outer plate, and the cover may be formed from a metallic core part and a polymeric overmold covering the core part. The polymeric overmold protects the core part, and reduces any sharp points or clicking if the hinge comes into contact with the other leg of the wearer, a brace worn on the other leg, or other objects.

In an embodiment of the rotation stop, the rotation stop may be a single unitary piece or in another embodiment the rotation stop may be defined by a plurality of interlocking components including, for example, an extension stop and a flexion stop which combine to form a rotation stop.

When defined by a plurality of components, the rotation stop comprises an extension stop and a flexion stop. The extension and flexion stops interlock and span a distance between the upper and lower hinge components. The extension stop defines a first aperture and the flexion stop defines a second aperture, such that the first and second apertures correspond to the two third location points and by interlocking are not prone to movement when in contact with the upper and lower components.

The extension and flexion stops are modular and may have unique geometries corresponding to different degrees of rotation for extension and flexion. For example, an extension stop may have a 40 degree limit and the flexion stop may have a 70 degree limit thereby having different degree configurations to one another.

The extension and flexion stops may be provided in a kit whereby any one of the extension stops, each corresponding to a different degree configuration, may interlock with any one of the flexion stops having different degree configurations. This allows for a highly modular hinge affording a multitude of different rotation stops for both flexion and extension. These features permit adjustability of the hinge over the course of treatment of a knee by allowing the wearer or caregiver to modify the extension and flexion stops, irrespective to one another, and hence the rotation of the knee.

In another variation of the rotation stop, the rotation stop defines an extension stop and a flexion stop such that the extension and flexion stops interlock with one another at a forward end of the flexion stop and a rearward end of the extension stop effectively forming a single unitary stop having defined geometries for both extension and flexion.

According to another embodiment, the rotation stop spans a distance defined between the geometries of the upper and lower hinge components. In a variation, the extension and flexion stops span a distance defined between the upper and lower hinge components, thereby confining the stops within the hinge and assuring contact with the peripheral surfaces of the upper and lower hinge components.

A clearance is defined between the outer plate and the rear component on a posterior side of the hinge. The clearance provides access to the extension and flexion stops so that they may be contained within the hinge as opposed to being mounted externally of the hinge.

In a variation of the hinge, the extension and flexion stops are contained between the outer plate and the rear component. However, it will be understood that in variations of the hinge that the stops may protrude outwardly (such as anteriorly or posteriorly) from the outer plate and rear component.

BRIEF DESCRIPTION OF THE DRAWINGS

The inventive orthopedic device is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

FIG. 2 is a schematic view showing the hinge according to FIG. 1 with an extension stop.

FIG. 3 is a schematic view showing the hinge according to FIG. 1 with an extension stop and a flexion stop.

FIG. 4 is an enlarged schematic view showing the hinge according to FIG. 1 with an extension stop and a flexion stop.

FIG. 12 is a schematic view of an interior surface of the cover according to FIG. 1.

FIG. 13 is a cross-sectional view of the cover taken along line XIII-XIII in FIG. 12.

DETAILED DESCRIPTION OF VARIOUS EMBODIMENTS

A. Overview

Figure 1:
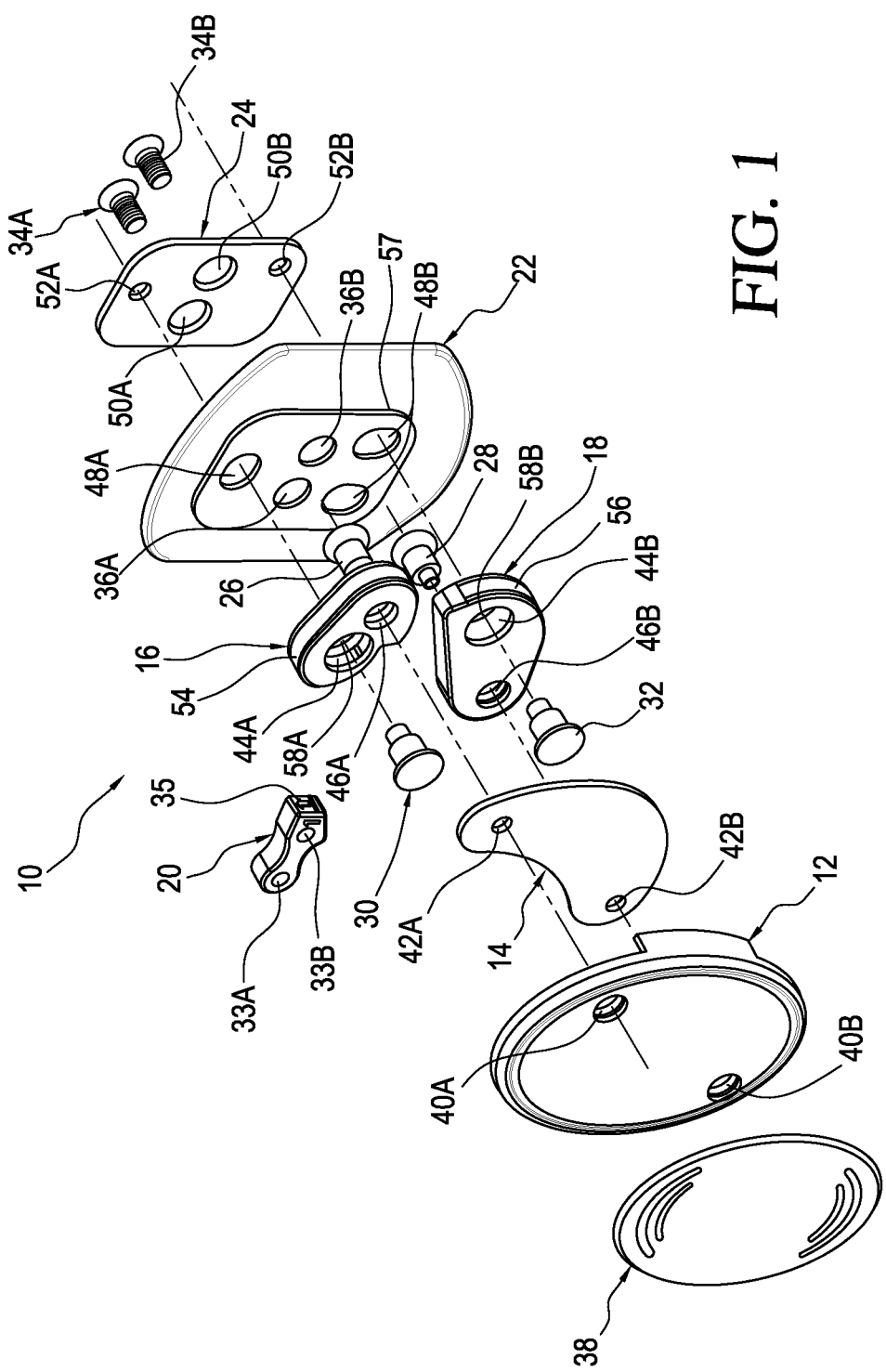
FIG. 1 is an exploded view showing an embodiment of a hinge in accordance with the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Hinge for Orthopedic Devices

FIG. 1 illustrates an exemplary embodiment of a hinge 10 for use in orthopedic devices, in particular a hinge adapted for use in a knee brace. The hinge 10 simulates the movement of a user's knee joint, while being capable of regulating its flexion and extension within a number of prescribed ranges of motion. This ability to simulate and regulate the knee joint movements within a selected optimal range of motion helps to rehabilitate an injured knee joint and may further prevent injury of the same due to hyperextension or flexion of the knee.

The hinge 10 includes upper and lower hinge components each including upper and lower covers 16, 18 secured to upper and lower parts of the orthopedic device (such as frame portions or hinge arms connecting to frame portions), respectively, and pivotally connected to an outer hinge component. The outer hinge component comprises an outer plate 14 having an arcuate rocker shape, and an inner hinge component including a condyle plate 22 and an inner plate 24. A means for controlling the extension of the hinge 10 is provided in the form of a rotation stop 20, exemplified in FIG. 1 by an extension stop, which is located between and meshes with the upper and lower hinge covers 16, 18 so as to engage the hinge covers upon a defined rotational degree associated with the rotation stop.

Upper and lower outer or exterior extending hinge fasteners 26, 28 extend through apertures 46A, 46B to connect to the upper and lower hinge covers 16, 18 to the outer plate 14 at upper and lower location points or apertures 42A, 42B and the outer plate 14 to a hinge cover 12 at location points or apertures 40A, 40B. Upper and lower inner or interior extending hinge fasteners 30, 32 extend through upper and lower recesses 44A, 44B and corresponding openings 58A, 58B formed by the upper and lower hinge covers 12, 14, respectively, through slots 48A, 48B formed by the condyle plate 22 and connect to the inner plate 24 at location points or apertures 52A, 52B.

A resilient material preferably forms the condyle plate 22 since it is used to provide support to the condyle region of the knee, and can yield slightly as the knee moves. The condyle plate 22 forms a retention area 57 form fitted for receiving the inner plate 24 from the inner side of the hinge (side adjacent the knee). The retention area 57 in combination with the inner plate 24, which is semi-rigid or rigid, provides added strength to the condyle plate 22 whereat it couples to the other components of the hinge. The areas outside the condyle plate 22 are resilient since the inner plate does not reinforce them. In use, the condyle plate receives a pad which covers the inner side of the condyle plate.

In reference to FIGS. 1 and 2, the hinge 10 includes upper and lower hinge arms 60, 62 mounted within upper and lower cover openings 54, 56 formed by the upper and lower hinge covers 16, 18, respectively. The fasteners extending through the upper and lower openings extend through the hinge arms as well.

Figure 11:
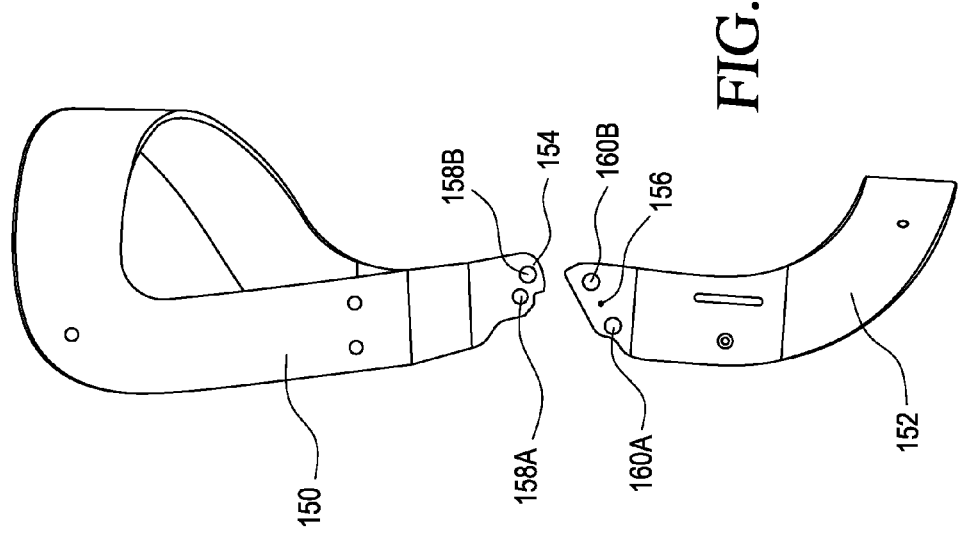
FIG. 11 is a schematic view of the knee brace frame according to FIG. 10 without the hinge.
Figure 10:
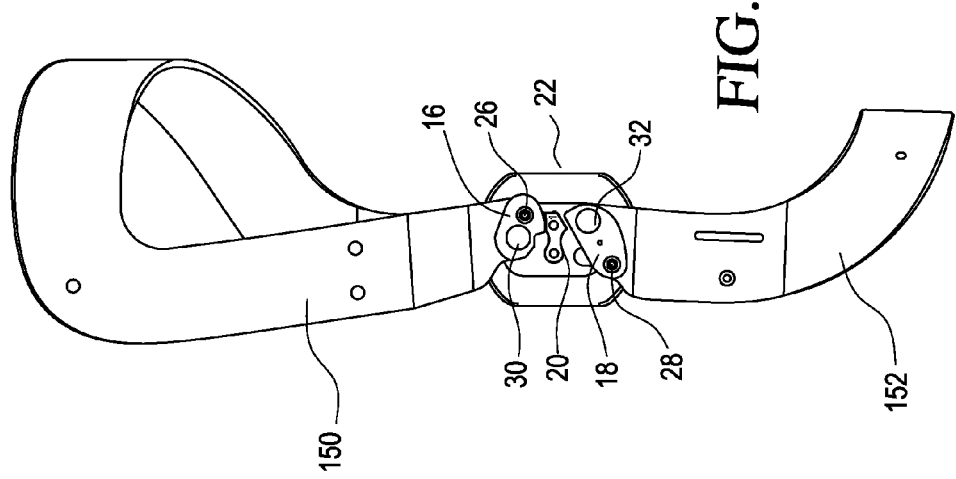
FIG. 10 is a schematic view of the hinge according to FIG. 1 without an outer plate and located on a knee brace frame.

As depicted in FIGS. 10 and 11, a variation of the hinge arms is depicted whereby the orthopedic device is exemplified as a knee brace having upper and lower frame portions 150, 152 defining end portions 154, 156, respectively, adapted for mounting to the hinge. According to one variation, the end portions 154, 156 are defined by the hinge arms 60, 62, as shown in FIG. 2, externally covered by carbon fiber composite material during a lamination process used for forming the orthopedic device frame. In another variation, the hinge arms 154, 156 are formed from a thermoplastic used to form the frame of the knee brace. In each of the variations, the hinge arms 154, 156 define apertures 158 (A, B), 160 (A, B), respectively which correspond to the apertures 46, 58 of the upper and lower hinge covers.

As shown in FIGS. 12 and 13, the hinge cover 12 has an interior side defining an interior recess 180 bordered by a wall 184 corresponding in shape to the outer plate 14. The outer plate 14 secures within the interior recess 180, and the apertures 40A, 40B defined by the hinge cover 12 correspond to the apertures 42 formed by the outer plate 14.

The hinge cover 12 includes a reinforcement plate 194 that is embedded into the hinge cover 12 so as to provide increased stiffness. The reinforcement plate 194 generally corresponds in shape to the outer plate 14, and provides reinforcement at least at the area of the recess 180. The reinforcement plate 194 is preferably embedded within the hinge cover 12 so as to assure that it cannot be removed. For example, it may embedded within the hinge cover during an injection molding process to form the hinge cover.

Various openings 186 are formed by the hinge cover 12 and are in correspondence with the interior recess 180, and are provided in part to allow venting of heat from the reinforcement plate when the hinge cover is molded. The hinge cover includes a section 178 that is not reinforced by the stiffer outer plate, and may be configured in some variations of the hinge cover to bend.

The hinge cover 12 defines a flange 182 protruding from the interior side 180 and is intended to abut or to be proximate to the condyle plate 22 when the hinge is assembled and located on the anterior side of the hinge. The flange 182 protects the internal components of the hinge on the anterior side of the hinge, and stiffens the hinge cover at such region. The posterior of the hinge is open in that a clearance is defined between the hinge cover and the condyle plate so as to permit removal and installation of the rotation stop.

The hinge cover 12 has an exterior side 188 defining an exterior recess 190 bordered by a wall 192 corresponding in shape to an indicia element 38, such as a sticker. The indicia element 38, as depicted in FIG. 1, is secured within the exterior recess 190. Grooves 196 may be formed along either of the interior or exterior sides of the hinge cover 12 so as to facilitate bending of the hinge cover in a prescribed direction based on the orientation of the grooves. This facilitated bending will minimize risk of the hinge tearing if it is caught onto an object due to the more rigid and stronger plates and fasteners secured thereto.

The hinge cover is preferably constructed from a polymeric material that may be glassed filled. The outer plate is preferably formed from a metal, such as stainless steel, or substantially rigid material, which when inserted into the interior recess, combines with the cover to form a substantially rigid and durable component that can withstand the shock, impact and other various forces endured when the brace is worn during physical activities. The polymeric covering greatly enhances sliding forces and acts as a buffer to the more rigid components underneath it.

According to a variation, the cover is molded about and over the outer plate so that the outer plate is tightly received by the interior recess. The openings 186 are therefore provided in part to relieve heat emanating from the outer plate when the polymeric material is molded about the outer plate to form the cover. In another variation, the cover may be molded prior to connecting the outer plate thereto, with the outer plate being snugly retained by the cover.

The hinge cover and outer plate are preferably secured to the hinge arms (via the hinge cover) of the brace with rivets for the fasteners 30, 32 so as to more permanently secure the components to one another. Likewise, the condyle plate and the inner plate are secured to the hinge arms (via the hinge covers) with rivets for the fasteners 26, 28 for the same reasons as with the hinge cover and outer plate.

The extension stop 20 is secured to the rear component via a pair of stop fasteners 34A, 34B mounted against the inner plate 24 and extending through apertures 50A, 50B defined by the inner plate 24 and apertures 36A, 36B formed by the condyle plate 22. Preferably, the stop fasteners 34A, 34B are fixably secured yet removable so as to permit replacement of the rotation stop. The rotation stop is arranged to prevent rotation of the upper and lower hinge covers (and the corresponding brace frames upon which they are attached) at a predetermined angle defined by the geometrical shape of the extension stop. The extension stop 20 may define indicia 35 to notify proper placement and alignment within the hinge, as in the case of an arrow pointing upwardly.

The arrangement of securing the extension stop 20 via at least two fasteners is that it provides a more secure fixation of the extension stop vis-à-vis the upper and lower hinge covers. Specifically, in known hinges, a single fastener is used to secure the extension stop which led to the extension stop having a tendency to spin about the fastener when forces are applied to the extension stop. Due to the possible movement of the extension stop, risk of adjustment of the extension stop may occur which leads to the extension stop at being arranged to stop the upper and lower hinge covers at an angle different from the predetermined angle that the extension stop is intended to stop.

The fasteners, in particular the stop fastener 34B in FIG. 2, are preferably located at a position between the upper and lower hinge covers so as to better balance the force against the extension stop. This results in a more stable rotation stop and further maintains the stop at the location which is desired to stop the upper and lower hinge covers. The geometry of the extension stop is more robust from the configuration often found in conventional extension stops, thereby further stabilizing the extension to a greater degree.

The hinge 10 is arranged to receive a plurality of different rotation stops including extension stops ranging from the preferable range of 0 to 40 degrees, or a combination of extension and flexion stops, with the flexion stops ranging from the preferable range of 0 to 90 degrees. In the example of FIG. 2, the hinge 10 is shown as having a rotation stop 64 including an extension stop 20 arranged to stop extension of the hinge at 0 degrees (beyond straightening the knee). Turning to the example of FIG. 3, a rotation stop 66 is defined by interlocking flexion and extension stops 68, 70, respectively, at 20 degrees. It will be pointed out that the extension and flexion stops can be combined with different degree configuration.

The geometrical configuration of the rotation stop determines the angular configuration described above, in particular the peripheral surface of the rotation stop in combination with the geometrical configuration of the peripheral surface of the hinge arm covers.

In reference to FIG. 4, the rotation stop 71 includes a flexion stop 72 at 10 degrees and an extension stop 74 at 10 degrees. As can be seen from FIG. 4, the flexion and extension stops 72, 74 are mounted so that the stop fasteners 34A, 34B are located between where the hinge arm covers abut. In particular, the flexion and extension stops combine to span a distance between the upper and lower hinge components so as to arrest movement of the upper and lower portions of the hinge at the prescribed flexion and extension rotation stop angle. Of additional importance is that since the flexion and extension stops are located between the hinge covers, the rotation stop providing control for both flexion and extension is located within the hinge as opposed to being provided along portions of the hinge outside of the hinge cover.

The flexion stop 72 defines an upper abutment surface 76 configured in shape to a bottom surface 88 of the upper hinge cover 16, and a lower abutment surface 78 configured in shape to an upper surface 90 of the lower hinge cover 18. The flexion stop 72 defines an anterior surface 84 (directed toward the anterior side of the hinge and orthopedic device) configured in shape to interlock with a posterior surface 86 of the extension stop 74. Further, the flexion stop 72 defines a posterior surface 92 arranged substantially vertical relative to the posterior side of the upper and lower hinge covers, and at least has a height spanning the distance between the lower and upper abutment surfaces 88, 90.

The extension stop 74 defines an upper abutment surface 80 configured in shape at the bottom surface 88 of the upper hinge cover 16, and a lower abutment surface 82 configured in shape to an upper surface 90 of the lower hinge cover 18. The extension stop 74 defines an anterior surface 94 arranged substantially vertical relative to the anterior side of the upper and lower hinge covers, and at least has a height spanning the distance between the lower and upper abutment surfaces 88, 90.

Figure 7:
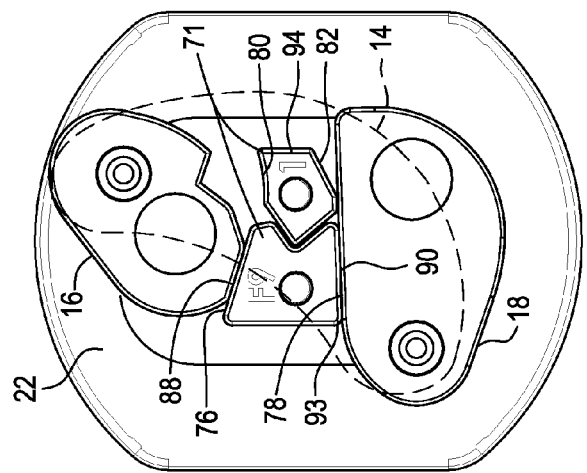
FIG. 7 is a schematic view showing the hinge according to FIG. 1 at a 90 degree flexion rotation.
Figure 6:
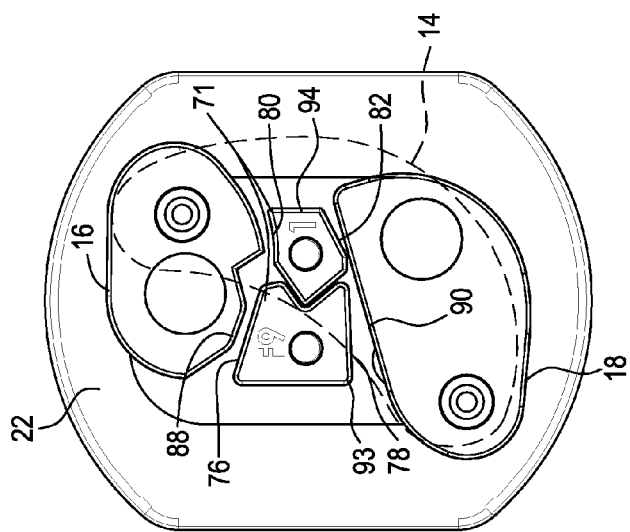
FIG. 6 is a schematic view showing the hinge according to FIG. 1 in a transition between 90 degree extension and 90 degree flexion.
Figure 5:
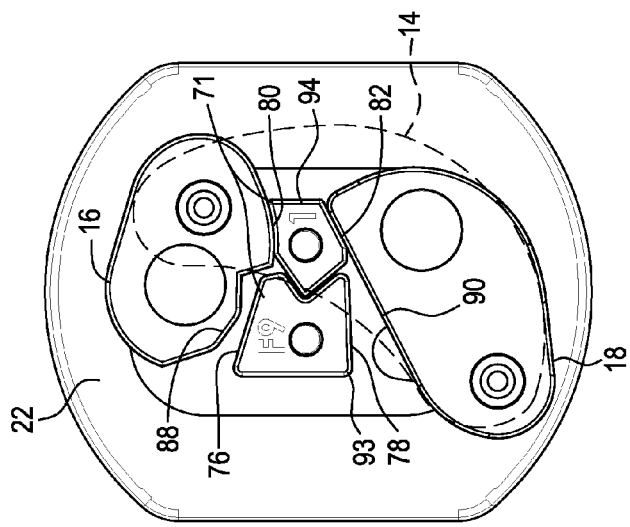
FIG. 5 is a schematic view showing the hinge according to FIG. 1 at a 90 degree extension rotation.

Turning to FIGS. 5-8, schematic views are provided of a hinge according to FIG. 1 with a flexion stop 93 at 90 degrees and an extension stop 94 at 10 degrees. FIG. 5 shows the hinge stopped at extension at 10 degrees, FIG. 6 shows the hinge in a transition between flexion and extension, and FIG. 7 shows the hinge stopped at flexion at 90 degrees.

Figure 8:
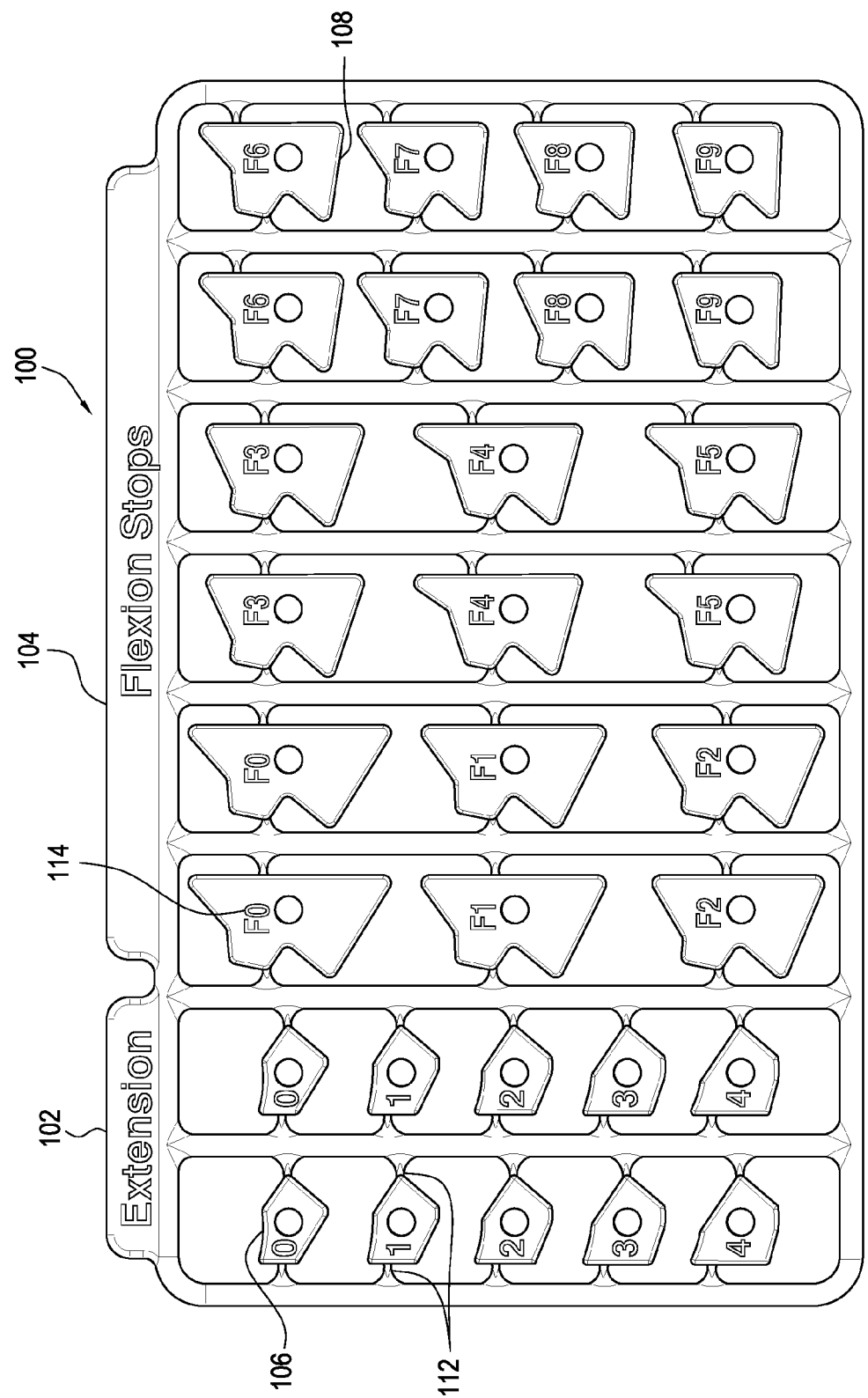
FIG. 8 is a schematic view showing a kit of extension and flexion stops having a plurality of different angular configurations.
Figure 9:
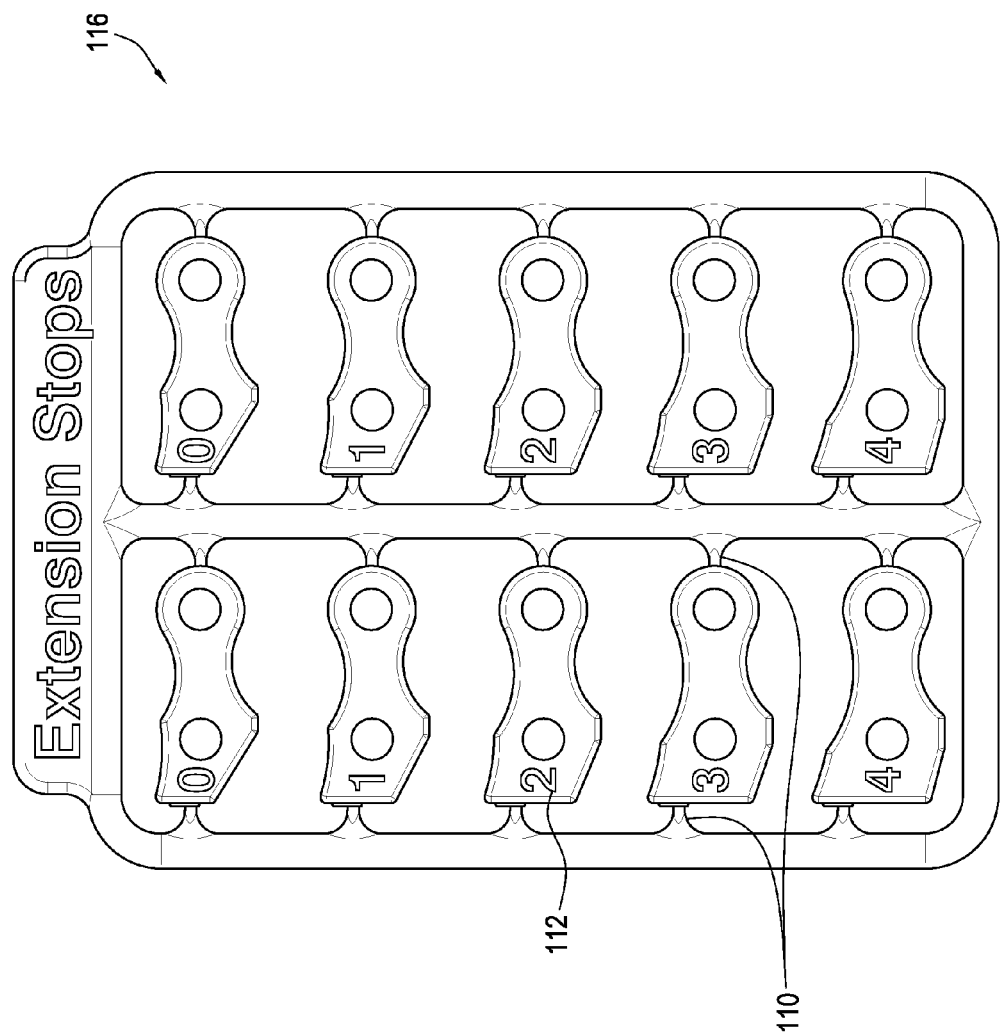
FIG. 9 is a schematic view showing a kit of extension stops having a plurality of different angular configurations.

In reference to FIGS. 8 and 9, the rotation stop can be provided as a kit 100 including a plurality of extension stops 102 and flexion stops 104 having a plurality of different degree configuration, or alternatively a kit 116 of just extension stops. Each of the extension and flexion stops 106, 108 have a general shape and are easily removable from the kit frame 110 via tabs 112, such that upon receipt of the kit, all of the individual stops are secured to the frame and are removable as needed. Preferably, the stops are formed from plastic and may be glass filled so that the kits can be molded the form depicted in FIGS. 8 and 9.

Each stop includes appropriate indicia 114 indicating the degree configuration. In the kit 100, the extension stops range from 0 to 40 degrees, and the flexion stops range from 0 to 90 degrees, with 10 degree increments. Because of their interlocking shapes, any one of the extension stops may be used in combination with any one of the flexion stops.

While the foregoing embodiments have been described and shown, it is understood that alternatives and modifications of these embodiments, such as those suggested by others, may be made to fall within the scope of the invention. While the orthopedic device has been described in the context of a knee brace, it will be understood that any of the principles described herein may be extended to other types of orthopedic devices.

The invention claimed is:

1. A hinge for an orthopedic device, comprising:
   an upper hinge component having a bottom peripheral surface defined by a first geometrical configuration;
   a lower hinge component having a top peripheral surface defined by a second geometrical configuration;
   an outer plate pivotally connected at first location points to the upper and lower hinge components;
   a rear component pivotally connected at second location points to the upper and lower hinge components;
   a rotation stop fixedly secured to the rear component in constant relative position between the rotation stop and the rear component and between the upper and lower hinge components, the rotation stop having a third geometrical configuration defining a top portion corresponding in shape to at least a portion of the bottom peripheral surface and arranged to directly abut the portion of the bottom peripheral surface, and a bottom portion corresponding in shape to at least a portion of the top peripheral surface and arranged to directly abut the portion of the top peripheral surface, the rotation stop secured to at least two third location points to the rear component;

wherein the rotation stop consisting of an extension stop and a flexion stop directly interlocking with one another at an anterior surface of the flexion stop and a posterior surface of the extension stop to make the rotation stop unitary, the extension stop is arranged to receive at least two different flexion stops, each having a different degree configuration, the flexion and extension stops combine to span a vertical distance between the upper and lower hinge components such that each of the flexion and extension stops contact the bottom peripheral surface of the upper hinge component and the top peripheral surface of the lower hinge component; and wherein the flexion and extension stops each consist of a singular integral element.

2. The hinge according to claim 1, further comprising a cover secured to and located adjacent to the outer plate.

3. The hinge according to claim 2, including a flange arranged on a forward side of the hinge, and extending to the rear component.

4. The hinge according to claim 2, wherein the cover defines a clearance between the rear component on a rear side of the hinge, the clearance providing access to the rotation stop.

5. The hinge according to claim 2, wherein the cover defines a recess receiving the outer plate.

6. The hinge according to claim 1, wherein the top peripheral surface is substantially linear.

7. The hinge according to claim 1, wherein a clearance is defined between the outer plate and the rear component on a posterior side, the clearance providing access to the extension and flexion stops.

8. The hinge according to claim 1, wherein the flexion stop defines an upper abutment surface configured in shape to a bottom surface of an upper hinge cover attached to the upper hinge component, and a lower abutment surface configured in shape to an upper surface of the lower hinge cover attached to the lower hinge component, the upper and lower abutment surfaces of the flexion stop having different contours from one another.

9. The hinge according to claim 8, wherein the flexion stop defines a posterior surface arranged substantially vertical relative to a posterior side of the upper and lower hinge covers.

10. The hinge according to claim 1, wherein the upper and lower hinge components are entirely spaced apart by the rotation stop.

11. The hinge according to claim 1, wherein the extension stop is secured to the rear component by at least one fastener extending through the extension stop.

12. The hinge according to claim 1, wherein the extension stop defines an upper abutment surface configured in shape to a bottom surface of an upper hinge cover attached to the upper hinge component, and a lower abutment surface configured in shape to an upper abutment surface configured in shape to an upper surface of the lower hinge component, the upper and lower abutment surfaces of the extension stop having different contours from one another.

13. The hinge according to claim 1, wherein the extension and flexion stops each having upper and lower abutment surfaces that are different from one another, the upper and lower abutment surfaces of the extension stop having a different shape from the upper and lower abutment surfaces of the flexion stop.

14. The hinge according to claim 1, wherein the extension and flexion stops combine to engage against an entirety of a segment of the bottom surface of the top component defined between a width of the rotation stop.

15. The hinge according to claim 1, wherein the rear component defines apertures through which stop fasteners extend for securing the extension and flexion stops to the rear component, the apertures located at a same height on the rear component.

16. A hinge for an orthopedic device, comprising:
an upper hinge component having a bottom peripheral surface defined by a first geometrical configuration;
a lower hinge component having a top peripheral surface defined by a second geometrical configuration;
an outer plate pivotally connected at first location points to the upper and lower hinge components;
a rear component pivotally connected at second location points to the upper and lower hinge components;
a rotation stop consisting of an extension stop and a flexion stop interlocking with one another at an anterior surface of the flexion stop and a posterior surface of the extension stop to make the rotation stop unitary, the extension and flexion stops forming a third geometrical configuration defining a top portion corresponding in shape to at least a portion of the bottom peripheral surface and arranged to directly abut the portion of the bottom peripheral surface, and a bottom portion corresponding in shape to at least a portion of the top peripheral surface and arranged to directly abut the portion of the top peripheral surface;
wherein the extension stop is arranged to receive at least two different flexion stops, each having a different degree configuration;
wherein the flexion and extension stops combine to span a vertical distance between the upper and lower hinge components at an anterior surface of the flexion stop and a posterior surface of the extension stop, such that each of the flexion and extension stops contact the bottom peripheral surface of the upper hinge component and the top peripheral surface of the lower hinge component.

17. The hinge according to claim 16, wherein the extension and flexion stops are each defined by a degree configuration irrespective of one another.

18. The hinge according to claim 16, wherein the flexion stop defines an upper abutment surface configured in shape to the bottom peripheral surface formed an upper hinge cover attached to the upper hinge component, and a lower abutment surface configured in shape to a top peripheral surface of the lower hinge cover attached to the lower hinge component, the upper and lower abutment surfaces of the flexion stop having different contours from one another.

19. The hinge according to claim 18, wherein the flexion stop defines a posterior surface arranged substantially vertical relative to a posterior side of the upper and lower hinge covers.

20. The hinge according to claim 16, wherein the upper and lower hinge components are entirely spaced apart by the rotation stop.

21. The hinge according to claim 16, wherein the extension stop is secured to the rear component by at least one fastener extending through the extension stop.

\* \* \* \* \*